United States Patent
Imai et al.

(10) Patent No.: US 11,389,166 B2
(45) Date of Patent: Jul. 19, 2022

(54) LIGATION DEVICE

(71) Applicant: FORCE ENGINEERING CO., LTD., Utsunomiya (JP)

(72) Inventors: Takanori Imai, Utsunomiya (JP); Takaki Sawahata, Utsunomiya (JP); Hiroshi Hirota, Utsunomiya (JP); Shinichi Kanno, Utsunomiya (JP); Shinichi Ono, Utsunomiya (JP); Tomoyuki Sawahata, Utsunomiya (JP); Tomohiro Murakami, Utsunomiya (JP); Tomoaki Higuchi, Utsunomiya (JP)

(73) Assignee: FORCE ENGINEERING CO., LTD., Utsunomiya (JP)

( * ) Notice: Subject to any disclaimer, the term of this patent is extended or adjusted under 35 U.S.C. 154(b) by 0 days.

(21) Appl. No.: 16/973,282

(22) PCT Filed: May 25, 2020

(86) PCT No.: PCT/JP2020/020566
§ 371 (c)(1),
(2) Date: Dec. 8, 2020

(87) PCT Pub. No.: WO2021/014745
PCT Pub. Date: Jan. 28, 2021

(65) Prior Publication Data
US 2021/0161535 A1    Jun. 3, 2021

(30) Foreign Application Priority Data
Jul. 22, 2019   (JP) .............. JP2019-134518

(51) Int. Cl.
*A61B 17/12*   (2006.01)
*A61B 17/04*   (2006.01)

(52) U.S. Cl.
CPC .... *A61B 17/12009* (2013.01); *A61B 17/0482* (2013.01)

(58) Field of Classification Search
CPC .............. A61B 17/12009; A61B 17/12; A61B 17/12013; A61B 17/0482; A61B 17/0487;
(Continued)

(56) References Cited

U.S. PATENT DOCUMENTS

| 3,877,434 A | 4/1975 | Ferguson et al. |
| 5,282,825 A * | 2/1994 | Muck ............ A01K 15/00 119/804 |

(Continued)

FOREIGN PATENT DOCUMENTS

| CN | 103462668 A | 12/2013 |
| JP | S61-37148 A | 2/1986 |

(Continued)

OTHER PUBLICATIONS

Aug. 18, 2020 Written Opinion issued in International Patent Application No. PCT/JP2020/020566.

*Primary Examiner* — Tan-Uyen T Ho
*Assistant Examiner* — Bridget E. Rabaglia
(74) *Attorney, Agent, or Firm* — Oliff PLC

(57) ABSTRACT

The ligation device includes a tubular body having a tubular shape and including a hollow part into which a string-shaped body can be inserted. The tubular body includes a proximal opening and a distal opening at a proximal end part and a distal end part, respectively. The proximal opening and the distal opening communicate with each other via a lumen of the tubular body. The side of a first end part of the string-shaped body can be inserted into the hollow part. The tubular body includes, on the distal end part, a locking part capable of locking the side of a second end part of the string-shaped body, after the string-shaped body is wound around the (Continued)

target, in a state where the first end part side of the string-shaped body is inserted into the lumen.

2 Claims, 14 Drawing Sheets

(58) Field of Classification Search
CPC .... A61B 17/12018; A61B 2017/12004; A61B 17/32056
USPC ................................ 606/148, 139, 144, 113
See application file for complete search history.

(56) References Cited

U.S. PATENT DOCUMENTS

| | | | | |
|---|---|---|---|---|
| 5,776,152 | A * | 7/1998 | Sekons | A61B 17/0469 606/139 |
| 5,797,928 | A * | 8/1998 | Kogasaka | A61B 17/0469 606/139 |
| 5,904,690 | A * | 5/1999 | Middleman | B25B 9/00 606/113 |
| 7,147,635 | B2 * | 12/2006 | Ciarrocca | A61B 17/32056 606/48 |
| 8,206,322 | B2 * | 6/2012 | Hubregtse | A61B 17/22 600/585 |
| 9,339,265 | B2 * | 5/2016 | Surti | A61B 17/0401 |
| 9,408,608 | B2 * | 8/2016 | Clark, III | A61B 90/39 |
| 2001/0041901 | A1 | 11/2001 | Furusawa | |
| 2005/0261708 | A1 | 11/2005 | Pasricha et al. | |
| 2007/0213745 | A1 | 9/2007 | Takemoto et al. | |
| 2013/0267965 | A1 | 10/2013 | Mizuguchi et al. | |
| 2014/0296901 | A1 * | 10/2014 | Derwin | A61B 17/3421 606/185 |

FOREIGN PATENT DOCUMENTS

| | | |
|---|---|---|
| JP | H07-51274 A | 2/1995 |
| JP | 2002-95667 A | 4/2002 |
| JP | 2005-329240 A | 12/2005 |
| JP | 2007-236679 A | 9/2007 |
| JP | 4414616 B2 | 2/2010 |
| JP | 5788893 B2 | 10/2015 |
| WO | 2012/046757 A1 | 4/2012 |

* cited by examiner

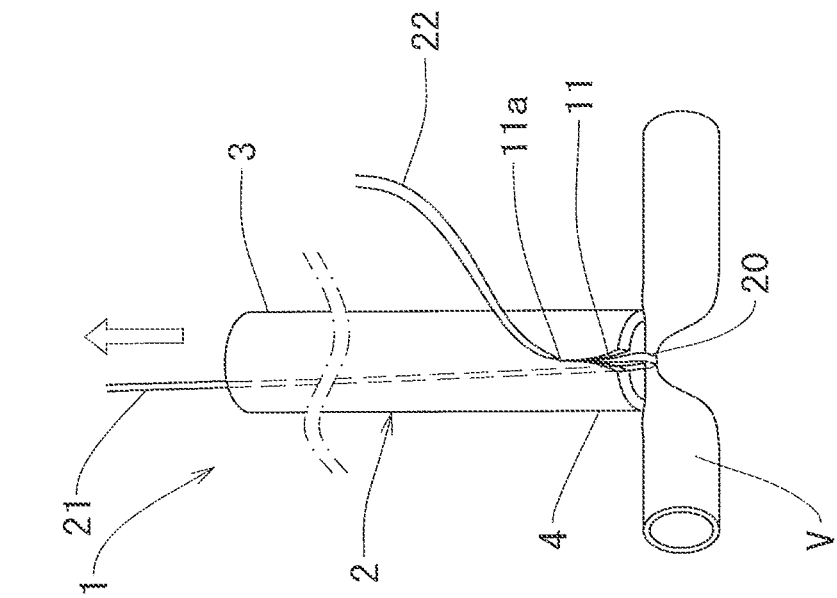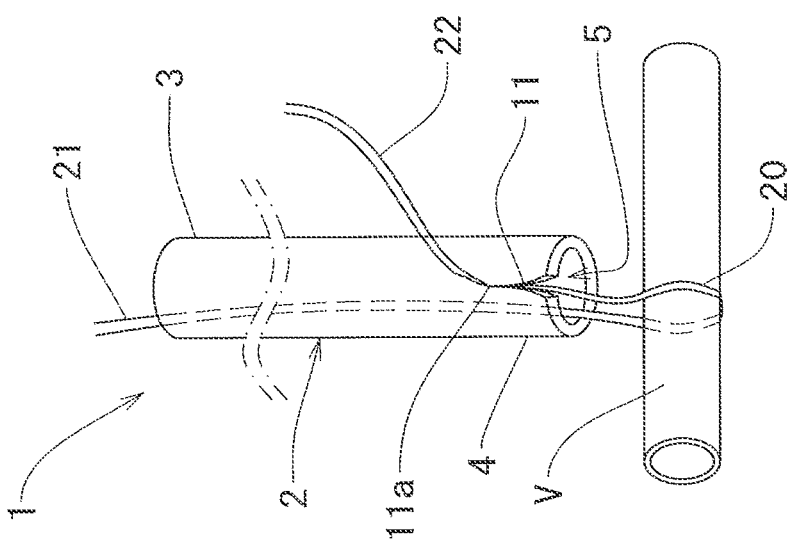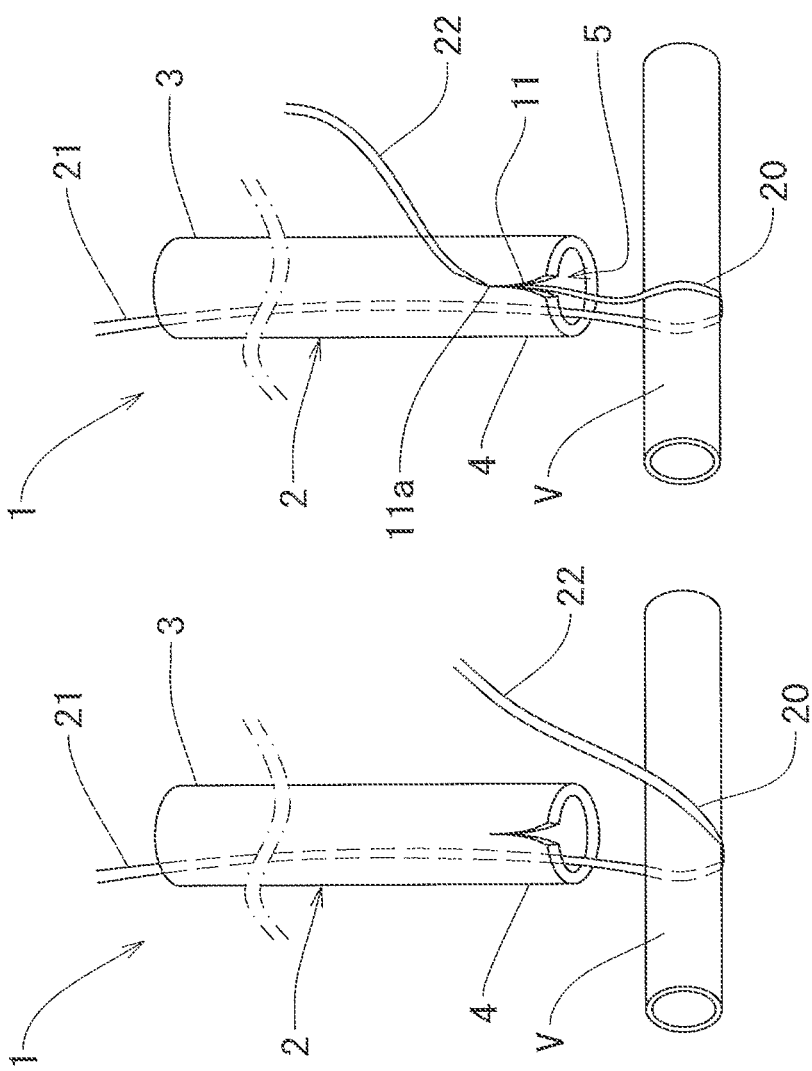

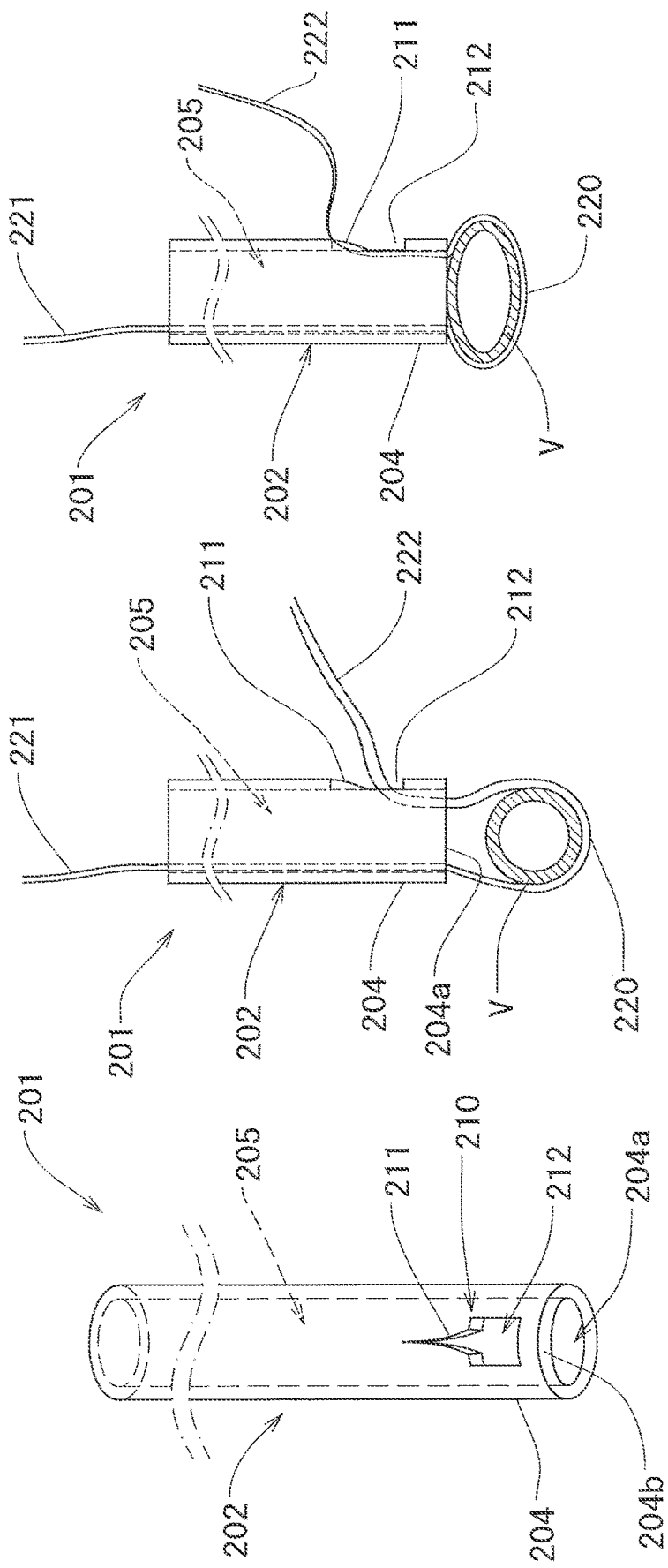

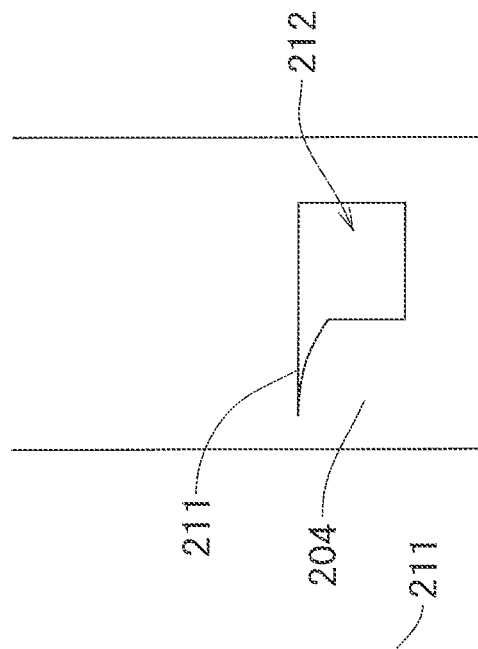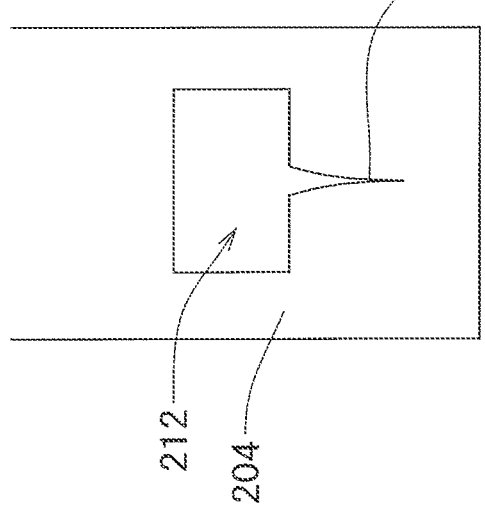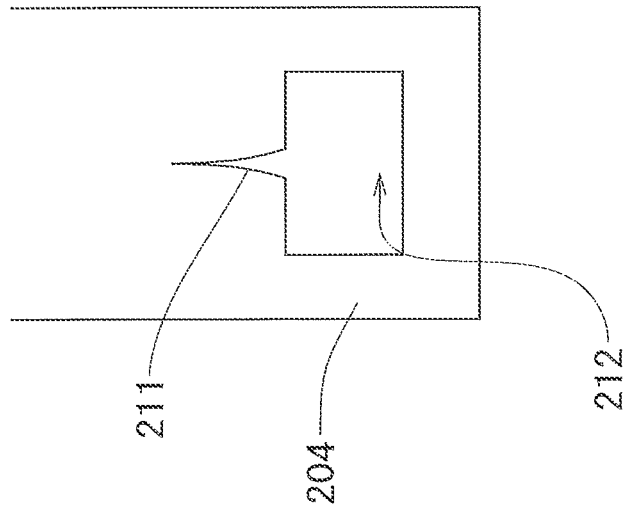

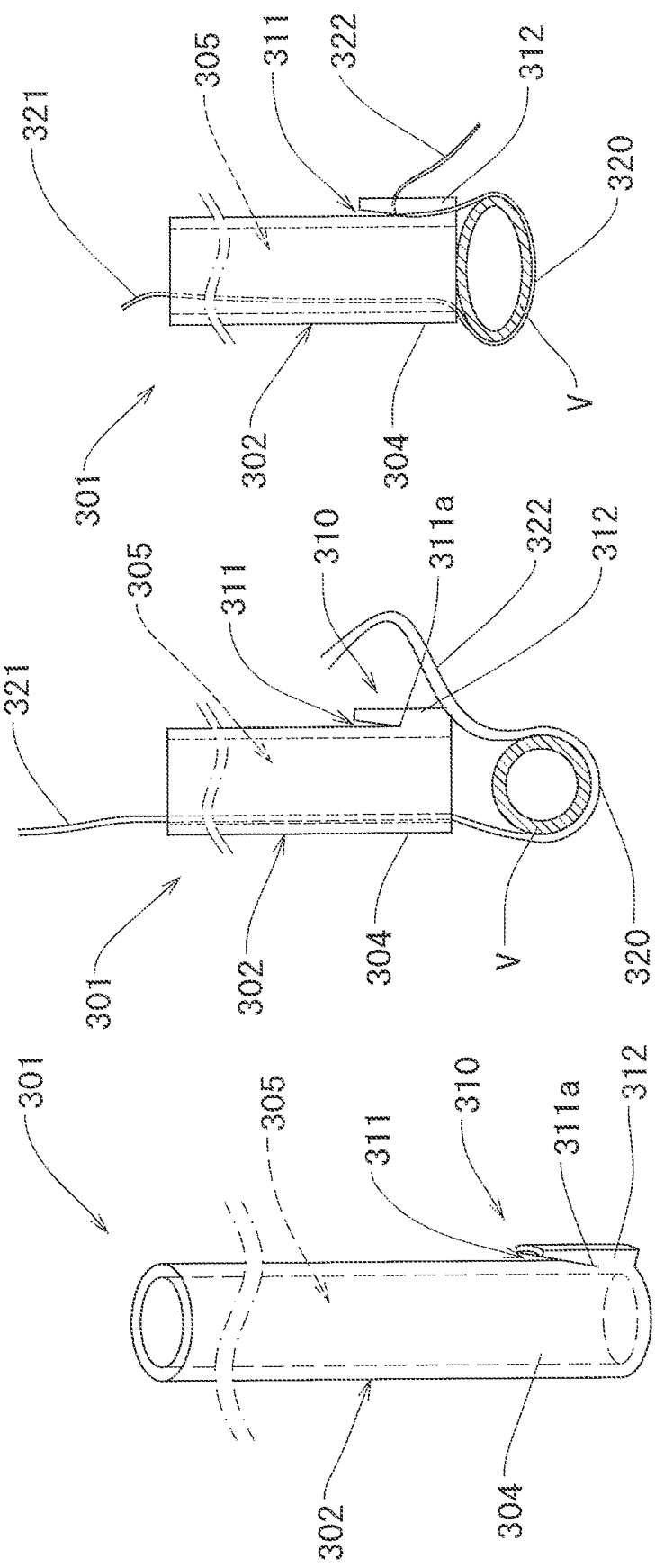

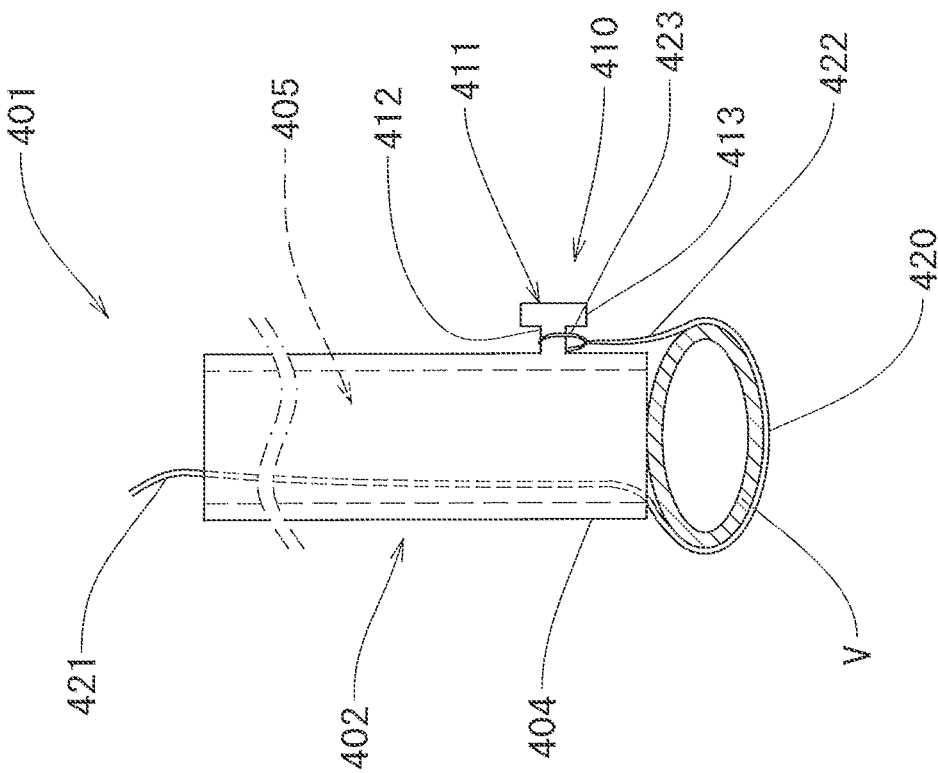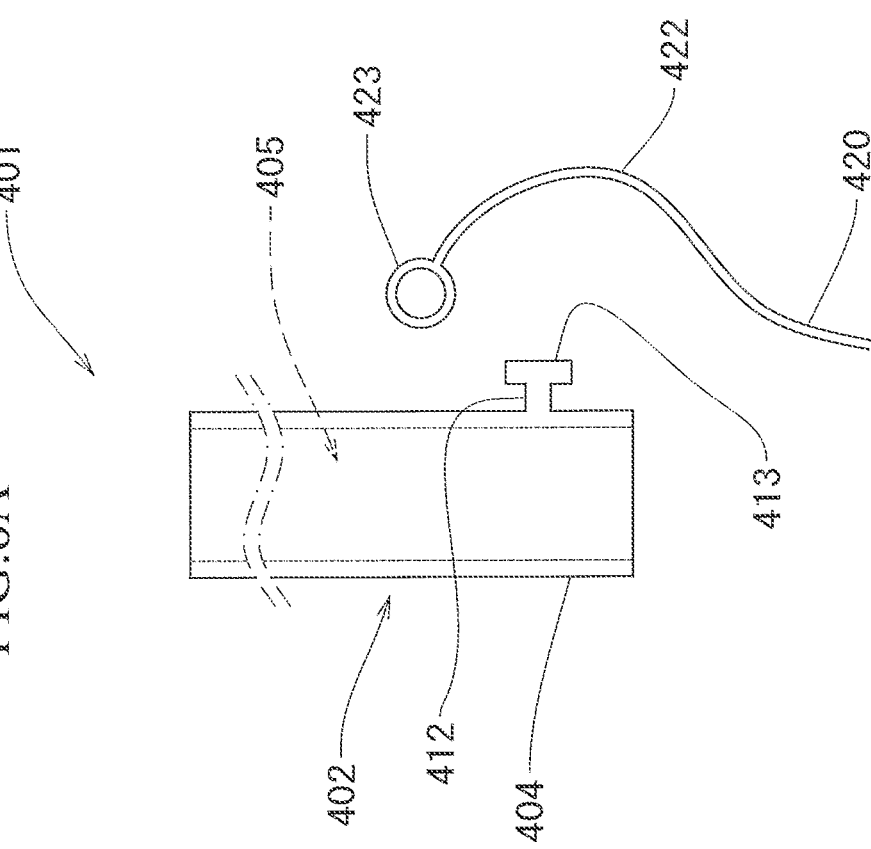

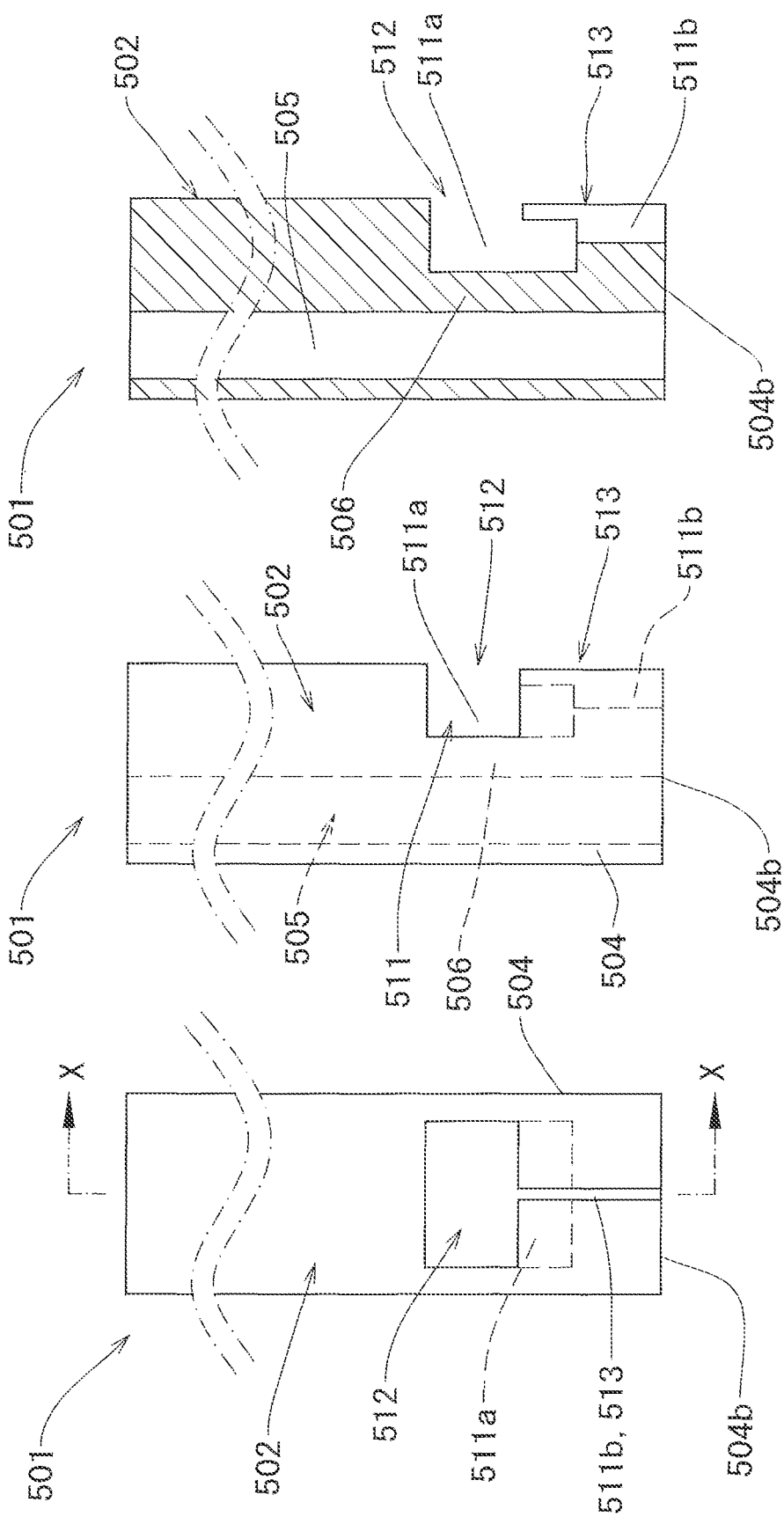

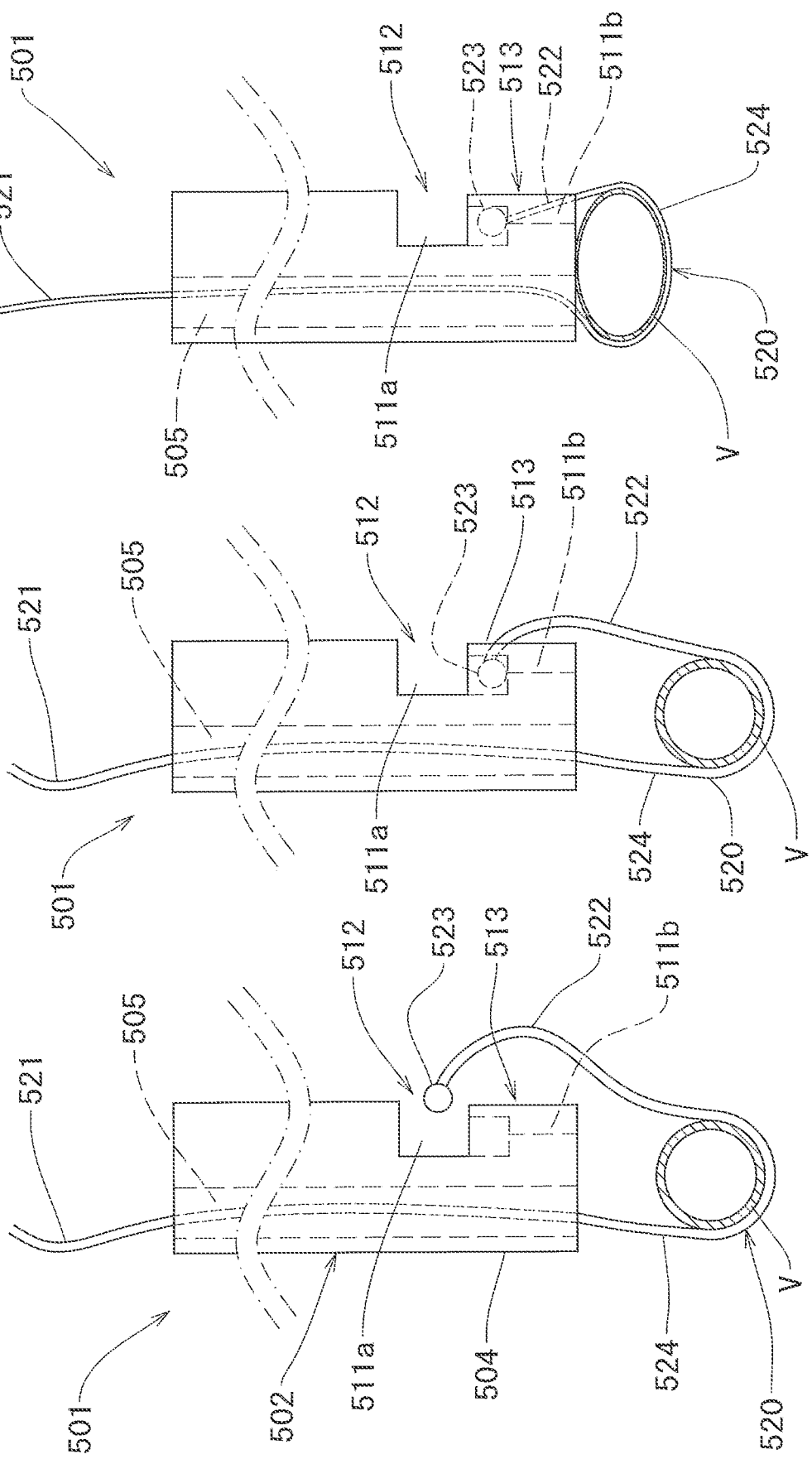

LIGATION DEVICE

TECHNICAL FIELD

The present invention relates to the technical field of a ligation device for ligating a living body vessel such as a blood vessel and an intestinal tract, an organ, an instrument, or the like in a surgical operation.

BACKGROUND ART

In various types of surgical operations, living body vessels such as blood vessels, intestinal tracts, and ureters may be temporarily ligated. For example, in Carotid Endarterectomy (CEA), when a narrowed artery is incised to remove plaque, the artery may be temporarily ligated to block blood flow. In Off-Pump Coronary Artery Bypass Grafting (OP-CABG), the coronary artery may be temporarily ligated when the bypass is anastomosed to the coronary artery. In addition to the blocking of living body vessels, various ligatures may be performed for the purpose of temporary suturing of organs and the like, fixation of instruments such as inserted catheters, cannulas, and shunte tubes, and securing of the surgical field. For example, in order to fix a catheter or the like inserted into a blood vessel, the catheter may be ligated with the blood vessel. Further, in the cannulation of an artificial heart-lung machine, in order to fix the blood feeding/blood removing cannulas, a purse suture may be provided around the insertion site and ligated after the cannula is inserted. Moreover, in stent graft interpolation for aortic aneurysm, a sheath may be ligated with the blood vessel to fix the sheath. For these various types of ligation, a ligation device called a tourniquet using a tubular body and a string-shaped body may be used (see Patent Literatures 1 to 4).

A general tourniquet is used as follows, when ligating a living body vessel, for example. First, a string-shaped body such as a surgical loop or a suture thread is wound around a living body vessel. Subsequently, both end parts of the string-shaped body are inserted from the distal end of the tubular body, and both end parts of the string-shaped body are pulled out from the proximal end of the tubular body. Further, in a state where the distal end part of the tubular body is pressed against the living body vessel while both end parts of the string-shaped body are pulled in the proximal direction, the string-shaped body is fixed to the proximal end part of the tubular body with forceps, a clip, or the like. In this way, the living body vessel can be ligated by using the wound string-shaped body and the tubular body. The strength of the ligation can be adjusted by releasing the fixation of the string-shaped body. Further, when fixing the cannula in the cannulation, a tourniquet can be used as follows, for example. A suture thread is wound in advance around the cannula insertion site of an organ or the like by using a suture needle, and both end parts of the string-shaped body are inserted into the tubular body. Then, by inserting the cannula and fixing the cannula to the tubular body by pulling the suture thread while pressing the tubular body against the insertion site of the cannula, the insertion site is crimped to the cannula and the cannula can be fixed.

In most cases, the tubular bodies used in such ligation devices have a total length of about several cm to several tens of cm and a diameter of about 5 to 10 mm. In particular, when the total length of the tubular body is long, it is difficult to perform a step of inserting both end parts of the string-shaped body into the tubular body and taking out both end parts of the string-shaped body from the tubular body by hand, or by using tweezers, forceps, and the like. Therefore, an instrument called a snare including a hook part at the distal end, such as the ligation device of Patent Literatures 1 to 3, may be used in this step. The two end parts of the string-shaped body can be pulled out from the proximal end of the tubular body by inserting the snare from the proximal end of the tubular body in a state where the string-shaped body is wound around the living body vessel, hooking both end sides of the string-shaped body to the hook part at the distal end of the tubular body, and pulling out the snare from the tubular body.

On the other hand, in the ligation device of Patent Literature 4, one end part of the string-shaped body is formed integrally with the tubular body in advance, and the other end part of the string-shaped body is inserted into the tubular body after the string-shaped body is wound around the living body vessel. Unlike Patent Literatures 1 to 3, after the string-shaped body is wound around the living body vessel, only the other end part of the string-shaped body needs to be inserted into the tubular body and taken out from the tubular body, so that it is comparatively easy to perform the work, even without using a snare.

CITATION LIST

Patent Literatures

Patent Literature 1: U.S. Pat. No. 3,877,434
Patent Literature 2: Japanese Patent No. 4414616
Patent Literature 3: Japanese Patent No. 5788893
Patent Literature 4: Japanese Patent Application Publication No. S61-37148

SUMMARY OF INVENTION

Technical Problem

A ligation device as described above is generally disposable including the snare, and if a device requiring a snare is used, the cost increases. Further, it is not preferable to increase the number of instruments used during surgery. Moreover, if one end part of the string-shaped body is fixed to the tubular body in advance, as in the ligation device of Patent Literature 4, the tubular body may become an obstacle when the string-shaped body is wound around the living body vessel, and thus, the degree of freedom of work is low. Therefore, it is desired to provide a ligation device having excellent workability without requiring a special instrument such as a snare, in particular by improving the shape of the tubular body, and this is the problem to be solved by the present invention.

Solution to Problem

The present invention has been devised in view of the above circumstances and with the object of solving the problems described above. The invention of claim 1 is a ligation device, wherein the ligation device includes a tubular body having a tubular shape and including a hollow part into which a string-shaped body can be inserted, the tubular body includes a proximal opening at a proximal end part and a distal opening at a distal end part, respectively, the proximal opening and the distal opening communicate with each other via the hollow part of the tubular body, the ligation device capable of ligating a target by fixation of the string-shaped body pulled in a proximal direction to the tubular body in a state where the string-shaped body is wound around a target and the target is pressed against a side of the distal end part of the tubular body, a side of a first end part of the string-shaped body can be inserted into the hollow part, and the tubular body includes, on the distal end part, a locking part capable of locking a side of a second end part of the string-shaped body, after the string-shaped body is wound around the target, in a state where the side of the first end part of the string-shaped body is inserted into the hollow part.

The invention of claim 2 is the ligation device according to claim 1, wherein the locking part includes a locking groove that locks the string-shaped body by press-fitting.

The invention of claim 3 is the ligation device according to claim 2, wherein the locking groove is provided from a distal end surface of the tubular body toward the proximal direction.

The invention of claim 4 is the ligation device according to claim 2, wherein a notch formed by cutting a peripheral surface of the tubular body is provided at the distal end part of the tubular body, the locking groove is provided from an end part of the notch, and the notch and the locking groove do not extend to the distal end surface of the tubular body.

The invention of claim 5 is the ligation device according to claim 1, wherein the locking part includes a protruding part protruding in an outer radial direction from an outer peripheral surface of the distal end part of the tubular body, and the protruding part can lock the side of the second end part of the string-shaped body.

The invention of claim 6 is the ligation device according to claim 5, wherein the protruding part includes a locking groove that locks the string-shaped body by press-fitting.

The invention of claim 7 is the ligation device according to any one of claims 1, 5, and 6, wherein the locking part includes a winding part onto which the side of the second end part of the string-shaped body can be wound and locked.

The invention of claim 8 is the ligation device according to claim 1, wherein the locking part includes a locking hollow part provided inside the tubular body, and the side of the second end part of the string-shaped body can be inserted into and locked in the locking hollow part.

The invention of claim 9 is the ligation device according to claim 8, wherein the locking hollow part includes a large diameter part on a proximal side and a small diameter part on a distal side having a smaller diameter than the large diameter part, the large diameter part and the small diameter part are continuously formed, and the small diameter part extends to a distal end of the tubular body.

The invention of claim 10 is the ligation device according to claim 8 or 9, wherein, on an outer periphery of the locking hollow part, an opening part having a large width is provided at a proximal side, a groove part having a narrow width is provided on a distal side, respectively, and the opening part and the groove part are continuously formed.

The invention of claim 11 is the ligation device according to claim 9, wherein, on an outer periphery of the locking hollow part, an opening part having a large width is provided at a proximal side, a groove part having a narrow width is provided on a distal side, respectively, the opening part and the groove part are continuously formed, and the groove part extends to a distal side of the large diameter part.

The invention of claim 12 is the ligation device according to any one of claims 1 to 11, wherein the tubular body includes a main body part having a tubular shape and an attachment body attached to a distal end part of the main body part, and the locking part is provided in the attachment body.

Advantageous Effects of Invention

According to the inventions of claims 1 to 2 and 5 to 9, only the side of the first end part of the string-shaped body needs to be inserted into the hollow part, and after the string-shaped body is wound around the target, the side of the second end part of the string-shaped body can be locked to the locking part, and thus, a ligation device that does not require a special instrument such as a snare and has excellent workability can be obtained.

According to the invention of claim 3, the locking part can be provided with a comparably simple structure referred to as a locking groove.

According to the invention of claim 4, cleavage of the distal end surface during ligation can be suppressed.

According to the invention of claim 10, the side of the second end part of the string-shaped body can be easily inserted into the locking hollow part.

According to the invention of claim 11, the groove part extends to the distal side of the large diameter part, and thus, the string-shaped body is prevented from falling off in the radial direction, and excellent workability can be obtained.

According to the invention of claim 12, the attachment body including the locking part may be separately manufactured and attached, and thus, the ligation device can be easily manufactured by using an existing tube or the like.

BRIEF DESCRIPTION OF DRAWINGS

FIGS. 2A to 2C are explanatory diagrams of a ligation method using the ligation device according to the first embodiment.

FIG. 4A is a perspective view of a ligation device according to a second embodiment, and FIGS. 4B and 4C are explanatory diagrams of a ligation method of the ligation device according to the second embodiment.

FIG. 5A is a front view of a locking part of the ligation device according to the second embodiment, and FIGS. 5B and 5C are front views of a modification of the locking part of the ligation device according to the second embodiment.

FIG. 6A is a perspective view of a ligation device according to a third embodiment, and FIGS. 6B and 6C are explanatory diagrams of a ligation method of the ligation device according to the third embodiment.

FIG. 8A is a side view before ligation and FIG. 8B is a side view of a ligated state when a string-shaped body including an annular part is used in the ligation device according to the fourth embodiment.

FIG. 11A is a front view, FIG. 11B is a side view, and FIG. 11C is an X-X cross-sectional view of the ligation device according to the fifth embodiment.

FIGS. 12A to 12C are explanatory diagrams of a ligation method using the ligation device according to the fifth embodiment.

FIG. 14A illustrates a state where an attachment part is not attached to the main body part, and FIG. 14B illustrates a state where the attachment part is not attached to the main body part.

DESCRIPTION OF EMBODIMENTS

Figure 1A:
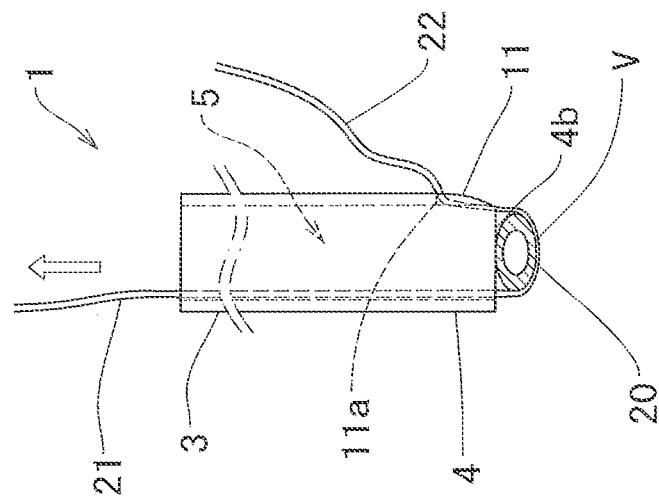
FIG. 1A is a perspective view of a ligation device according to a first embodiment.
Figure 3A:
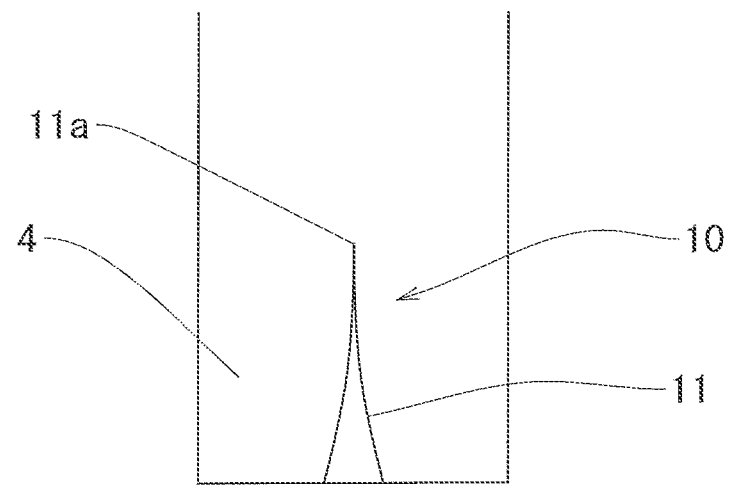
FIG. 3A is a front view of a locking part of the ligation device according to the first embodiment.

A first embodiment of the present invention will be described with reference to FIGS. 1 to 3. In the figures, reference numeral 1 denotes a ligation device used for ligating a living body vessel, for example, a blood vessel V, which is a target of the ligation. A ligation device 1 includes a long hollow tubular body 2 having a cylindrical shape. The tubular body 2 includes a proximal opening 3a and a distal opening 4a at a proximal end part 3 and a distal end part 4, respectively. The proximal opening 3a and the distal opening 4a communicate with each other inside the tubular body 2, and the inside of this communicating hollow portion forms a hollow part 5.

The tubular body 2 according to the present embodiment is formed of a synthetic resin material having elasticity and flexibility. The tubular body 2 may be colored. Different colors can be chosen, for example, if used for arteries, the tubular body 2 may be color-coded red, and if used for veins, the tubular body 2 may be color-coded blue. Alternatively, the tubular body 2 may be transparent or translucent. Further, only one of the end parts may be colored, or the end parts may be colored differently from the other parts so that the proximal end part 3 and the distal end part 4 can be easily distinguished. The tubular body 2 is not necessarily limited to a cylindrical shape, and various shapes such as a flat shape, a square tubular shape, and a tapered shape can be adopted. Moreover, the shapes of the inner circumference and the outer circumference of the tubular body 2 may be different from each other. For example, the outer circumference of the tubular body 2 may have a circular shape, while the inner circumference of the tubular body 2 may have a polygonal shape.

The tubular body 2 includes, at the distal end part 4, a locking part 10 capable of locking a string-shaped body 20 that is wound around a target. The locking part 10 in the present embodiment is a locking groove 11 provided by cutting in a proximal direction from a distal end surface 4b of the tubular body 2. The locking groove 11 is provided to penetrate the inner and outer circumferences of the tubular body 2, and a groove bottom 11a is formed narrower than the thickness of the string-shaped body 20. The string-shaped body 20 is inserted into the locking groove 11 from the side of the hollow part 5 toward the outside and pulled in the proximal direction (to the side of the groove bottom 11a) so that the string-shaped body 20 is press-fitted into and locked in the locking groove 11.

Figure 3B:
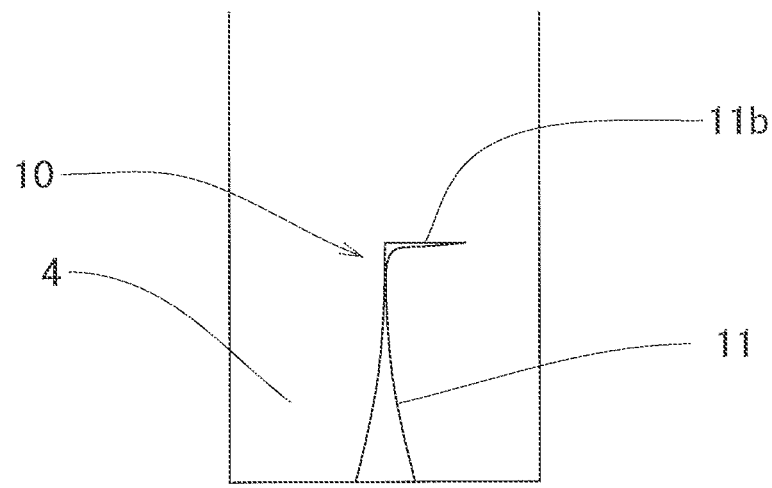
FIG. 3B is a front view of a modification of the locking part of the ligation device according to the first embodiment.

The shape of the locking groove 11 in the present embodiment is an inverted V shape that is narrower toward the groove bottom 11a. However, any groove shape into which the string-shaped body 20 can be locked may be used, for example, a notch having a linear shape. Alternatively, as illustrated in FIG. 3B, a hook shape may be used in which the locking groove 11 includes a hook part 11b cut in the circumferential direction. By shifting the distal end and the proximal end of the locking groove 11 in the circumferential direction in this way, it is possible to suppress the string-shaped body 20 from falling off. Other groove shapes include a curved groove shape or a groove provided with a folded structure. Further, the number of the locking groove 11 is not necessarily limited to one, and a plurality of the locking grooves 11 may be provided.

The string-shaped body 20 is formed of a stretchable synthetic resin material and has a flat string shape having a width that allows for insertion into the hollow part 5. The string-shaped body 20 has a structure having no difference between the two end parts, and during ligation, an end part on the side inserted into the hollow part 5 is referred to as a first end part 21, and an end part on the side locked into the locking part 10 is referred to as a second end part 22. However, differences may be provided in the structures of the two end parts, including a case where a bulging part, an annular part, or the like is provided, as described later. Further, the first end part 21 of the string-shaped body 20 may be provided with a hard part that is harder than the other parts so that the first end part 21 can be easily inserted into the hollow part 5. In this case, it is preferable that the hard part has a length equal to or longer than the length of the tubular body 2 in a length direction.

An appropriate structure of the string-shaped body 20 can be adopted depending on the target to be ligated. For example, a non-stretchable suture thread may be used as the string-shaped body 20, and the material and thickness of the non-stretchable suture thread can be chosen appropriately. Further, the shape of the string-shaped body 20 is not limited to a flat shape, and an appropriate shape such as a shape having a circular cross section or an elliptical shape can be adopted. Further, an appropriate length of the string-shaped body 20 can be chosen. However, it is necessary to wind the string-shaped body 20 around the target and insert the string-shaped body 20 into the tubular body 2, and thus, the string-shaped body 20 needs to be at least longer than the tubular body 2.

Figure 1B:
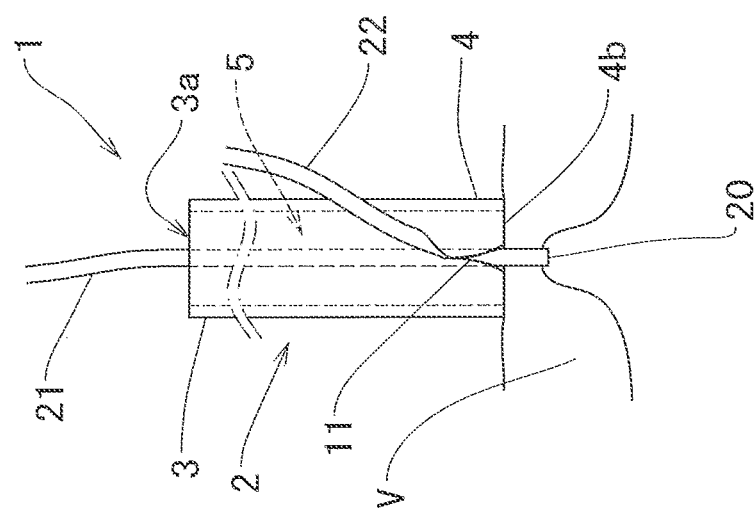
FIG. 1B is a front view of a ligated state of the ligation device according to the first embodiment.
Figure 1C:
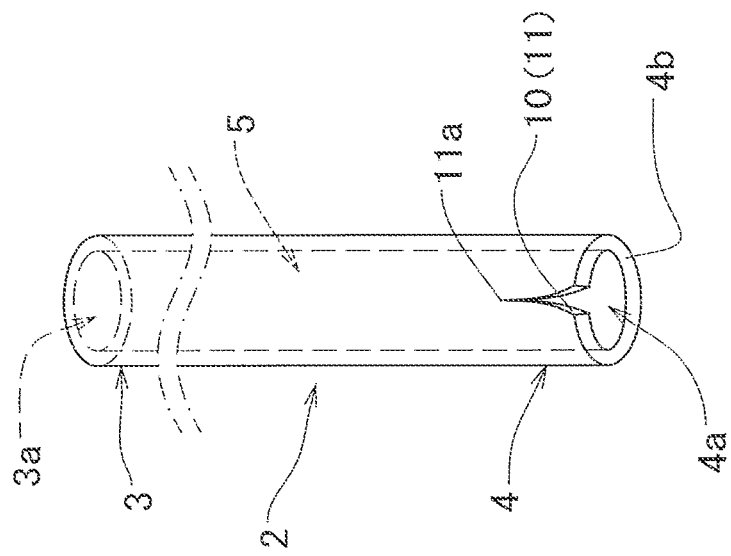
FIG. 1C is a side view of a ligated state of the ligation device according to the first embodiment.

Next, an example of a usage method of the ligation device 1 according to the first embodiment configured in this way will be described with reference to FIGS. 1 and 2. First, the first end part 21 of the string-shaped body 20 is inserted into the hollow part 5 from the distal opening 4a of the tubular body 2 of the ligation device 1, and is pulled out from the proximal opening 3a. In conjunction therewith, on the side of the distal end part 3, the string-shaped body 20 is wound an appropriate number of times around the blood vessel V, which is the target to be ligated (state of FIG. 2A). In FIG. 2A, the winding is performed as one annular part, but the winding may be performed a plurality of times. Then, the side of the second end part 22 of the string-shaped body 20 is inserted into the locking groove 11 from the side of the hollow part 5 toward the outside and pulled to the side of the groove bottom 11a, and thus, the side of the second end part 22 of the string-shaped body 20 is press-fitted into and locked in the locking groove 11 (state of FIG. 2B). Then, while the side of the exposed first end part 21 of the string-shaped body is pulled into the proximal direction, the distal end surface 4b of the tubular body 2 is pressed against the blood vessel V (states of FIGS. 1B, 1C, and 2C). In a state where the tubular body 2 is pressed against the blood vessel V with an appropriate force, the side of the first end part 21 of the string-shaped body 20 is fixed to the proximal end part 3 of the tubular body 2 by fixing means such as forceps or a clip (not illustrated). Thereby, the ligation of the blood vessel V is completed.

The winding of the blood vessel V by the string-shaped body 20 and the insertion of the string-shaped body 20 into the hollow part 5 may be performed in any order. After the string-shaped body 20 is wound around the blood vessel V, the string-shaped body 20 may be inserted into the hollow part 5, or the blood vessel V may be wound in a state where the string-shaped body 20 is inserted into the hollow part 5 in advance. If the string-shaped body 20 is inserted into the hollow part 5 in advance, it is not necessary to insert the string-shaped body 20 into the tubular body 2 after winding the blood vessel V, and thus, the operability is excellent. On the other hand, in a case where the tubular body 2 may become an obstacle when the string-shaped body 20 is wound around the blood vessel V, the string-shaped body 20 may be inserted into the hollow part 5 after winding the string-shaped body 20 around the blood vessel V. Alternatively, in a state where the string-shaped body 20 is locked to the locking part 10 in advance, the string-shaped body 20 may be wound around the blood vessel V, and then the side of the first end part 21 of the string-shaped body 20 may be inserted into the hollow part 5. In this way, ligation is possible in any order using the ligation device according to the present invention, and thus, the degree of freedom of the work is high. Similarly, in the following embodiments, ligation is possible in any order.

In the example of the above-mentioned usage method, the target is the blood vessel V and the string-shaped body 20 is wound around the outer circumference of the blood vessel V. However, the process of winding a string-shaped body around a target is not necessarily limited to the winding around the entire outer circumference of the target. That is, even if a surface layer portion of a blood vessel, an organ, or the like is sutured with a suture thread, it can be said that the string-shaped body is wound around the surface layer portion.

In the ligation device 1 according to the first embodiment described above, the tubular body 2 includes the locking part 10 capable of locking the side of the second end part 22 of the string-shaped body 20 in a state where the side of the first end part 21 of the string-shaped body 20 is inserted into the hollow part 5. Thus, only the side of the first end part 21 of the string-shaped body 20 needs to be inserted into the hollow part 5, so that compared to a ligation device in which both end parts of the string-shaped body 20 need to be inserted into the hollow part 5, the string-shaped body 20 can be easily inserted without requiring a special instrument such as a snare. Moreover, after the string-shaped body 20 is wound around the blood vessel V (target), the side of the second end part 22 of the string-shaped body 20 can be locked to the locking part 10, and thus, the workability is excellent.

The locking part 10 includes the locking groove 11 into which the string-shaped body 20 is press-fitted and locked, and the locking groove 11 is provided from the distal end surface 4b of the tubular body 2 toward the proximal direction. According to this configuration, the locking part can be provided with a comparably simple structure, and thus, the cost effectiveness is excellent.

Next, a second embodiment of the present invention will be described with reference to FIGS. 4 and 5. In the embodiments described below, mainly the structure of the distal end part of the tubular body including the locking part is different from that of the first embodiment. Other configurations and modifications are similar to those of the first embodiment, and thus, description thereof will be omitted as appropriate.

A tubular body 202 of a ligation device 201 according to the second embodiment is provided with a notch 212 obtained by cutting out a part of the outer peripheral surface of a distal end part 204. The notch 212 penetrates the inside and outside of the tubular body 202, but does not extend to a distal end surface 204b. Further, a locking groove 211 is provided at the proximal end of the notch 212 in the proximal direction. The locking groove 211 is similar to the locking groove 11 of the first embodiment, but the position of the opening is different. Thus, a locking part 210 according to the present embodiment includes the notch 212 and the locking groove 211.

A usage method of the ligation device 201 configured in this way can be, for example, as follows. First, a string-shaped body 220 is wound around the blood vessel V and a state where the side of a first end part 221 of the string-shaped body 220 is inserted into a hollow part 205 is obtained. Then, the side of a second end part 222 of the string-shaped body 220 is pulled to the outside from a distal opening 204a via the notch 212 (state of FIG. 4B). Further, while the side of the second end part 222 is pulled to the proximal side, the second end part 222 is press-fitted into the locking groove 211 and locked to the locking groove 211 (state of FIG. 4C). Then, in a state where the tubular body 202 is pressed against the blood vessel V with an appropriate force, the side of the first end part 221 of the string-shaped body 220 is fixed to the tubular body 202 to complete the ligation.

According to the ligation device 201, the locking groove 211 and the notch 212 do not extend to the distal end surface 204b as the distal end of the tubular body 202, and thus, the distal end surface 204b is not cleaved even when the tubular body 202 is pressed against the blood vessel V, and the blood vessel V can be stably pressed.

In order to suppress as much as possible a deformation of the distal end part 204 when the distal end part 204 is pressed against the blood vessel V, it is preferable that the notch 212 is separated from the distal end surface 204b. However, from the viewpoint of workability when the string-shaped body 220 is inserted into the notch 212, it is not preferable that the notch 212 is separated too much from the distal end surface 204b. Further, if the opening of the notch 212 is small, the deformation of the distal end part 204 can be suppressed, but if the opening is large, the workability is better. These features can be appropriately designed according to the material of the tubular body, the target to be ligated, and the like.

The locking groove 211 does not necessarily have to be provided at the proximal end of the notch 212. It is possible to adopt any groove shape into which the string-shaped body 220 can be locked, for example, the locking groove 211 may be provided in the distal direction from the distal end of the notch 212 as illustrated in FIG. 5B, or the locking groove 211 may be provided in an outer peripheral direction from a peripheral end of the notch 212 as illustrated in FIG. 5C. Further, a plurality of the locking grooves 211 may be provided.

Next, a third embodiment of the present invention will be described with reference to FIGS. 6A to 6C. In a ligation device 301 according to the third embodiment, a locking part 310 is provided on an outer peripheral part of a distal end part 304 of a tubular body 302. The locking part 310 includes a protruding part 312 protruding in an outer radial direction from the outer peripheral surface of the distal end part 304. The protruding part 312 has a structure in which a distal side is continuous with the outer peripheral surface of the tubular body 302, while a proximal side is inclined so as to gradually separate from the outer peripheral surface of the tubular body 302. That is, by providing the protruding part 312, a locking groove 311 having an open proximal side is formed between the protruding part 312 and the tubular body 302. By inserting a string-shaped body 320 into the locking groove 311 and press-fitting the string-shaped body 320 into a groove bottom part 311a on the distal side, it is possible to lock the string-shaped body 320.

A usage method of the ligation device 301 configured in this way can be, for example, as follows. First, the string-shaped body 320 is wound around the blood vessel V and a state where the side of a first end part 321 of the string-shaped body 320 is inserted into a hollow part 305 is obtained. Then, the side of a second end part 322 of the string-shaped body 320 is pulled out to the outer peripheral side of the tubular body 302 (state of FIG. 6B). Then, the side of the second end part 322 of the string-shaped body 320 is inserted into the locking groove 311 and press-fitted toward the groove bottom part 311a to lock the string-shaped body 320 in the locking groove 311 (state of FIG. 6C). Then, in a state where the tubular body 302 is pressed against the blood vessel V with an appropriate force, the side of the first end part 321 of the string-shaped body 320 is fixed to the tubular body 302 to complete the ligation.

The locking groove 311 according to the present embodiment is provided with an open proximal side in the distal direction, but the groove shape and direction are not necessarily limited thereto. The locking groove may be provided in the proximal direction or may be provided in the circumferential direction. Further, a plurality of the protruding parts 312 and a plurality of the locking grooves 311 may be provided.

Figure 7B:
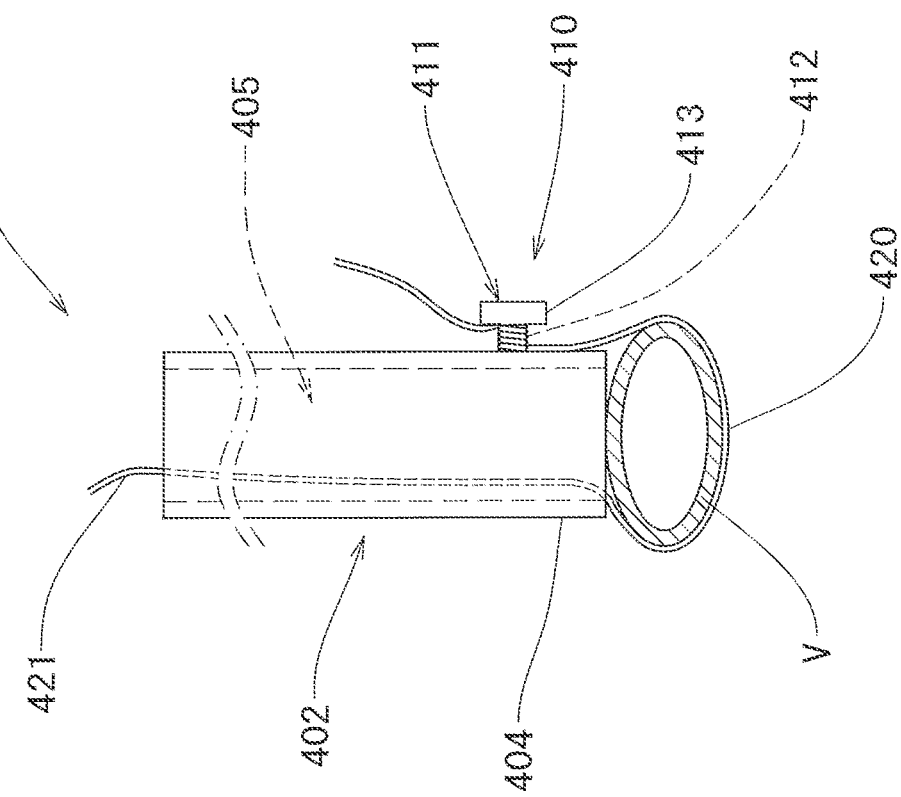
FIG. 7B is a side view of a ligated state of the ligation device according to the fourth embodiment.
Figure 7A:
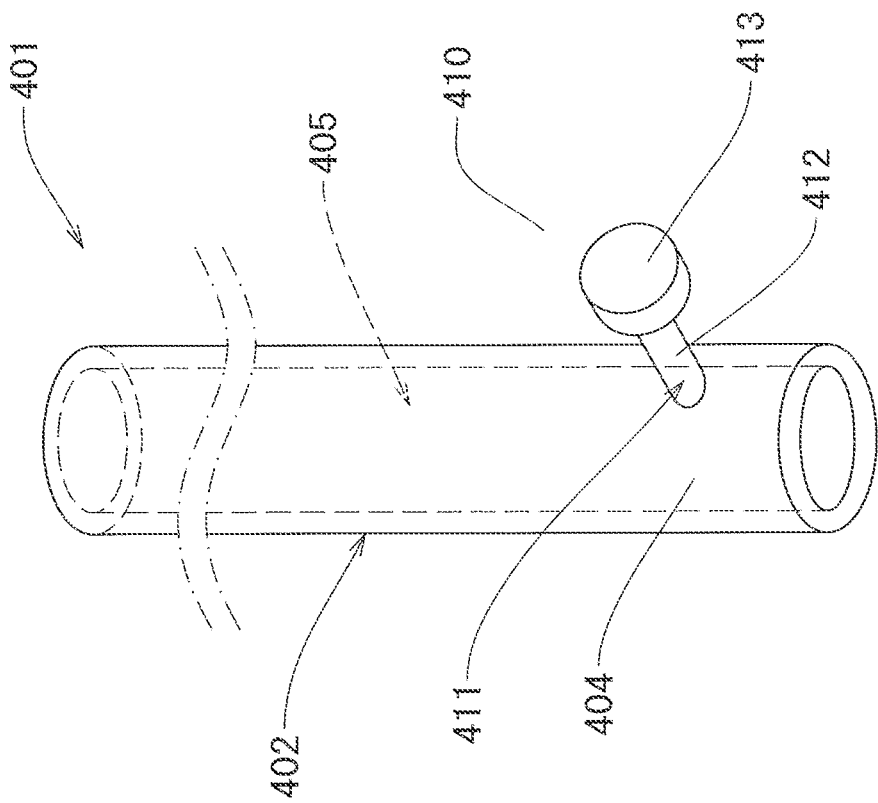
FIG. 7A is a perspective view of a ligation device according to a fourth embodiment.

Next, a fourth embodiment of the present invention will be described with reference to FIGS. 7 to 9. In a ligation device 401 according to the fourth embodiment, a locking part 410 is provided on an outer peripheral part of a distal end part 404 of a tubular body 402. The locking part 410 is a winding part 411 as a protruding part protruding outward from the outer periphery of the distal end part 404. The winding part 411 is integrally provided with the tubular body 402 and forms a T-shape including a leg part 412 extending outward from the outer circumference of the distal end part 404 and a head part 413 provided on the outer end side of the leg part 412 in a direction perpendicular to the leg part 412. As will be described later, a string-shaped body 420 is wound around the leg part 412, and the head part 413 can achieve the function of preventing the wound string-shaped body 420 from falling off, and the function of pressing the string-shaped body 420 between the head part 413 and the tubular body 402 to lock the string-shaped body 420.

A usage method of the ligation device 401 configured in this way can be, for example, as follows. First, the string-shaped body 420 is wound around the blood vessel V and a state where the side of a first end part 421 of the string-shaped body 420 is inserted into a hollow part 405 is obtained. Then, the side of a second end part 422 of the string-shaped body 420 is pulled out to the outer peripheral side of the tubular body 402, and is wound around the winding part 411 several times to be locked. Then, in a state where the tubular body 402 is pressed against the blood vessel V with an appropriate force, the side of the first end part 421 of the string-shaped body 420 is fixed to the tubular body 402 to complete the ligation.

The string-shaped body 420 may be locked by crossing the string-shaped body 420 during the winding to prevent unwinding of the string-shaped body 420, or the string-shaped body 420 may be locked by being sandwiched and pressed between the tubular body 402 and the head part 413 to prevent unwinding of the string-shaped body 420. Alternatively, the string-shaped body 420 may be prevented from unwinding by winding the string-shaped body 420 not only around the leg part 412 but also around the head part 413 from a plurality of directions. Further, a locking groove may be provided in the winding part 411, and after winding the string-shaped body 420 around the winding part 411, the string-shaped body 420 may be press-fitted into the locking groove to lock the string-shaped body 420.

Further, as illustrated in FIGS. 8A and 8B, if an annular part 423 is provided on the side of the second end part 422 of the string-shaped body 420, the string-shaped body 420 does not necessarily have to be wound around the leg part 412. In this case, if the head part 413 is inserted into the annular part 423 and the annular part 423 is attached to the leg part 412, the head part 413 prevents the string-shaped body 420 from falling off, and the string-shaped body 420 can be locked to the winding part 411. The annular part 423 configured in this way may be formed in advance at the time of manufacturing the string-shaped body 420, or may be provided by forming a connection or the like at the side of the second end part 422 when the string-shaped body 420 is used.

Figure 9A:
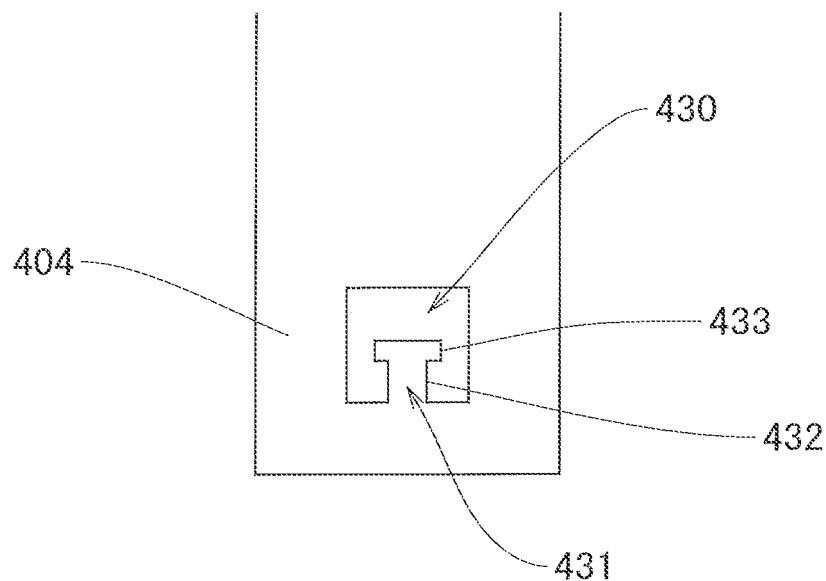
FIGS. 9A and 9B are front views of a modification of the ligation device according to the fourth embodiment.
Figure 9B:
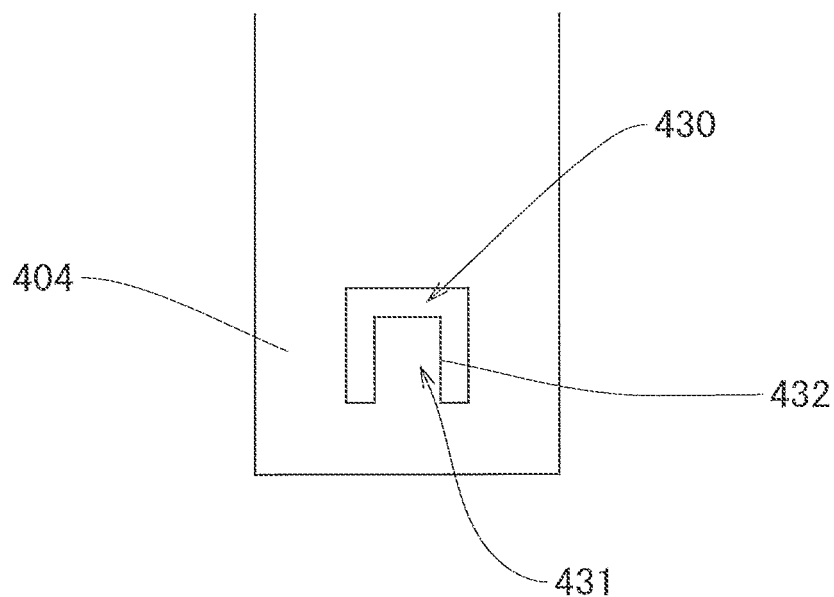
Figure 10:
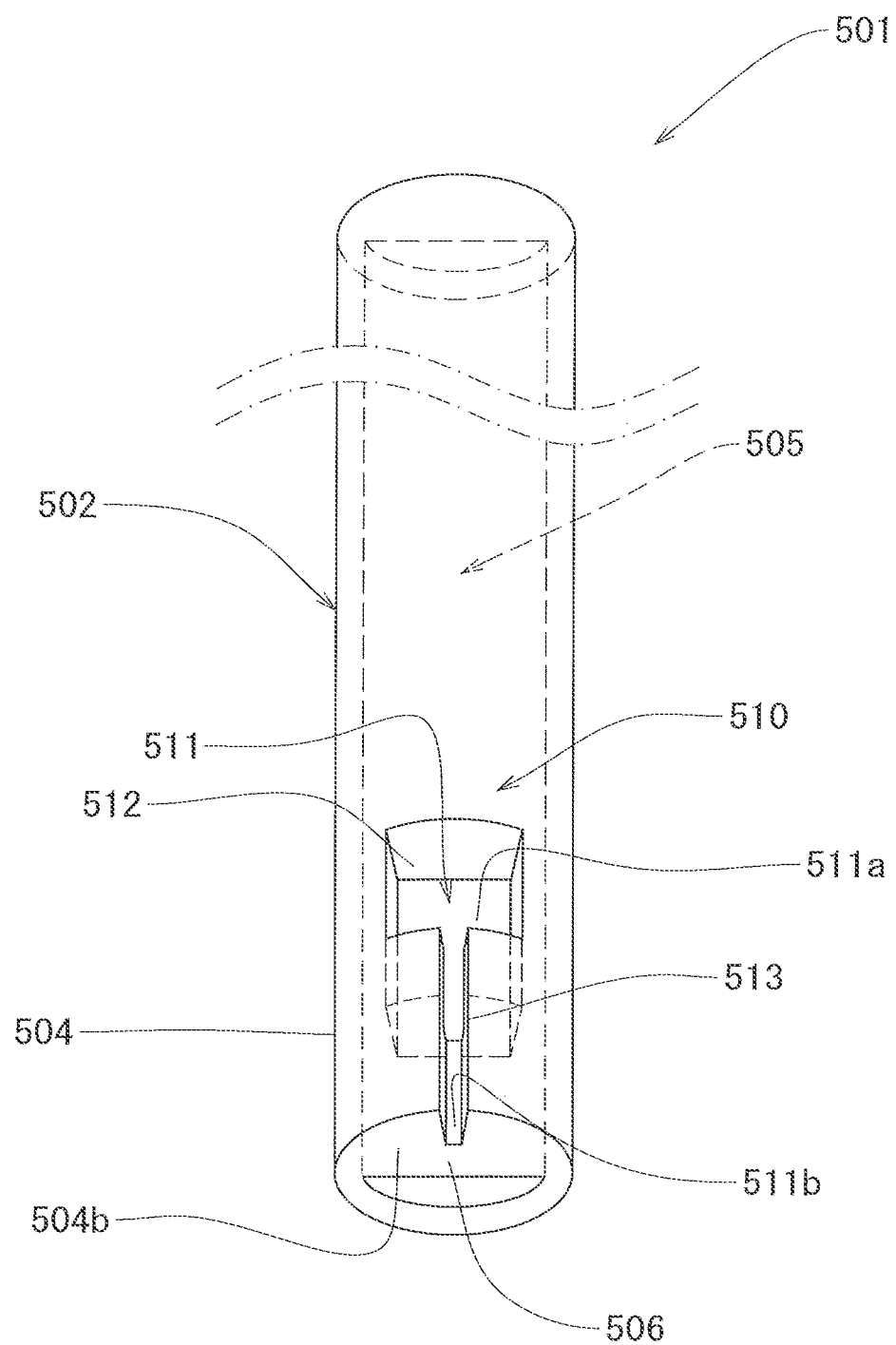
FIG. 10 is a perspective view of a ligation device according to a fifth embodiment.

FIGS. 9A and 9B illustrate modifications of the fourth embodiment. The winding part 411 according to the embodiment described above is provided as a protruding part protruding outward from the outer periphery of the distal end part 404, but in the modification, a winding part 431 of the locking part 410 is provided by cutting out a portion of the outer peripheral surface of the distal end part 404. That is, as illustrated in FIG. 9A, a notch 430 having a substantially inverted U-shape is provided to penetrate the inside and outside of the distal end part 404, and the winding part 431 is formed by a protruding part protruding from the distal end of the notch 430 in the proximal direction. The winding part 431 forms a T-shape including a leg part 432 extending from the distal end of the notch 430 in the proximal direction, and a head part 433 extending perpendicularly to the leg part 432 from the proximal end part of the leg part 432.

In the present modification, the side of the second end part 422 of the string-shaped body 420 may be wound around the leg part 412 of the winding part 431 in the notch 430, to be locked to the leg part 412. The head part 433 achieves a function of preventing falling off, similar to the fourth embodiment described above. Further, in a case where the annular part 423 is provided on the side of the second end part 422 of the string-shaped body 420, as illustrated in FIG. 9B, the winding part 431 may only include the leg part 412, and may not include the head part 413.

Next, a fifth embodiment of the present invention will be described with reference to FIGS. 10 to 13. In a ligation device 501 according to the fifth embodiment, a locking part 510 including a hollow part is provided at a distal end part 504 of a tubular body 502. The hollow part of the locking part 510 is a locking hollow part 511, and the locking hollow part 511 is provided so as to be separated from a hollow part 505 through which a first end part 521 of a string-shaped body 520 is inserted, by a partition part 506. By providing the partition part 506, the hollow part 505 is provided in a semicircular shape in a plan view.

The locking hollow part 511 has a configuration in which a large diameter part 511*a* on the proximal side and a small diameter part 511*b* on the distal side having a smaller diameter than the large diameter part 511*a* are continuously formed. Further, on the outer peripheral surface of the locking hollow part 511, an opening part 512 having a wide width is provided on the distal side, and a groove part 513 is provided so as to extend from a distal end of the opening part 512 to a distal end surface 504*b* of the tubular body 502, and both the opening part 512 and the groove part 513 communicate with the locking hollow part 511. More specifically, the opening part 512 is provided on the proximal side of the large diameter part 511*a*, and the groove part 513 is provided on the distal side of the large diameter part 511*a* and in the small diameter part 511*b*. By providing the groove part 513 so as to extend to the large diameter part 511*a* in this way, it is possible to prevent the string-shaped body 520 from falling off to the outside as described later.

The string-shaped body 520 used in the ligation device 501 includes a bulging part 523 that bulges outward from a string part 524 as another part, on the side of a second end part 522. The bulging part 523 according to the present embodiment has a spherical shape, can be inserted into the large diameter part 511*a* of the locking hollow part 511 from the opening part 512, and can move in the proximal and distal directions in the large diameter part 511*a*, but is designed to have an appropriate size and hardness so that the bulging part 523 cannot be inserted into the groove part 513 and the small diameter part 511*b*. On the other hand, the string part 524 can be inserted into the groove part 513 and the small diameter part 511*b*. The bulging part 523 may be provided at an end part of the string-shaped body 520, or may be provided partway along the string-shaped body 520.

A usage method of the ligation device 501 configured in this way can be, for example, as follows. First, the string-shaped body 520 is wound around the blood vessel V and a state where the side of the first end part 521 of the string-shaped body 520 is inserted into the hollow part 505 is obtained. Then, the bulging part 523 provided on the side of the second end part 522 of the string-shaped body 520 is inserted into the large diameter part 511*a* from the opening part 512 (state of FIG. 12A). Then, the string-shaped body 520 is pulled to an appropriate position to move the bulging part 523 to the distal side of the large diameter part 511*a* and cause the bulging part 523 to abut against the proximal end of the small diameter part 511*b* (state of FIG. 12B). In conjunction therewith, the string part 524 on the side of the first end part 521 near the bulging part 523 is inserted from the groove part 513 into the locking hollow part 511 (state of FIG. 12C). At this time, the groove part 513 is positioned on the outer periphery of the large diameter part 511*a* on the distal side, and thus, the bulging part 523 is prevented from falling off to the outside by the groove part 513 and the small diameter part 511*b*. As a result, the side of the second end part 521 of the string-shaped body 520 is locked. Subsequently, the side of the first end part 521 is further pulled to obtain an appropriate state where the distal end surface 504*b* abuts and presses against the blood vessel V, and in this state, the side of the first end part 521 is fixed to the tubular body 502 to complete the ligation.

Figure 13A:
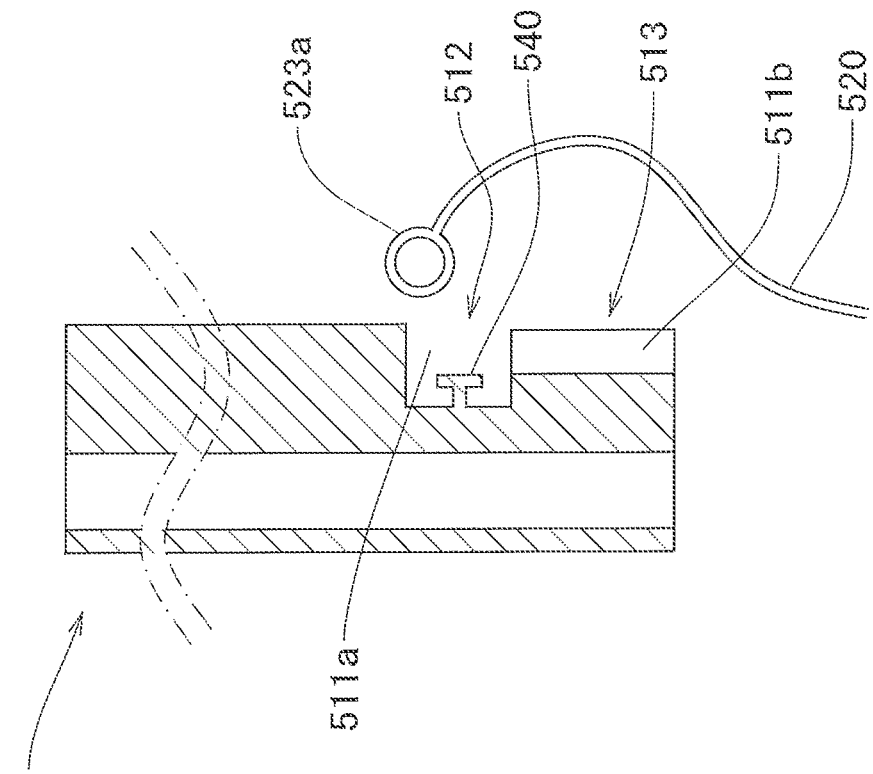
FIGS. 13A and 13B are cross-sectional views of a modification of the ligation device according to the fifth embodiment.

As a modification of the present embodiment, as illustrated in FIG. 13A, a structure may be adopted in which a narrow width part 530, into which the bulging part 523 can be inserted by applying a certain force, is provided between the proximal part side and the distal part side of the large diameter part 511*a*. The narrow width part 530 also prevents the bulging part 523 in the large diameter part 511*a* from falling off in the proximal direction.

Figure 13B:
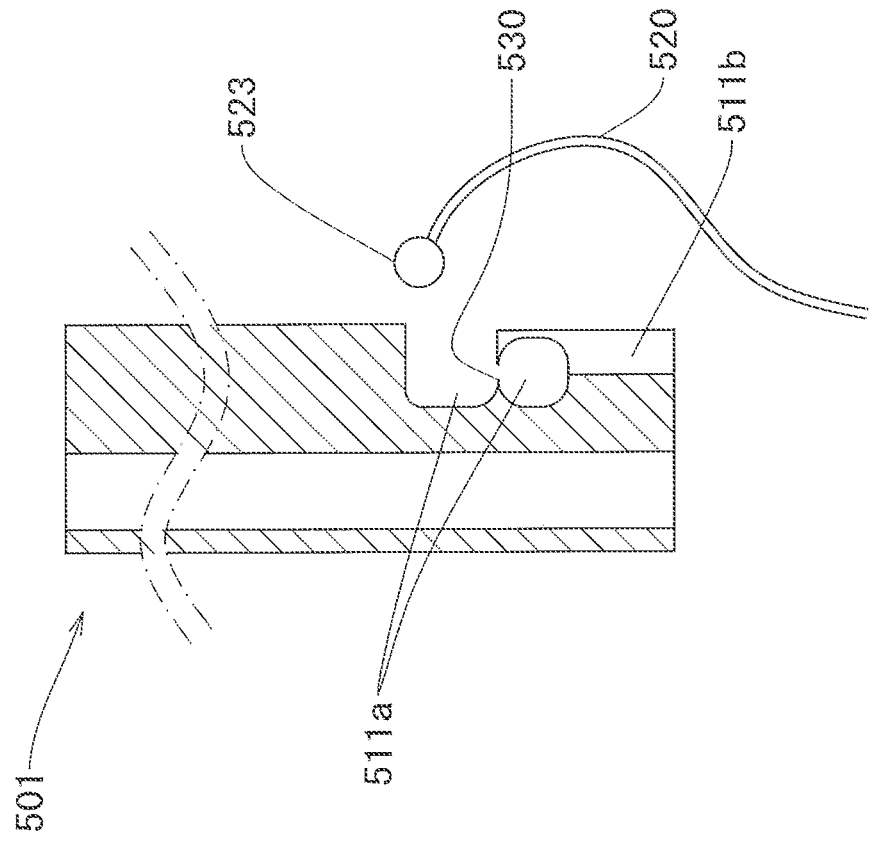

As another modification of the present embodiment, as illustrated in FIG. 13B, a T-shaped protruding part 540 may be provided in the large diameter part 511*a*. Then, an annular part 523*a* can be provided on the bulging part 523 of the string-shaped body 520, and the side of the second end part 521 can be locked by attaching the annular part 523*a* to the protruding part 540. In this case, the annular part 523*a* is prevented from falling off by the T-shape of the protruding part 540, and thus, it is not necessary that the groove part 513 extends to the large diameter part 511*a*.

In the ligation device according to each of the above embodiments, the side of the first end part of the string-shaped body can be inserted into the hollow part of the tubular body in advance. According to this ligation device, it is not necessary to insert any one of the end parts of the string-shaped body into the hollow part during surgery. That is, the side of the first end part of the string-shaped body is inserted into the hollow part in advance, and thus, it is not necessary to insert the string-shaped body into the tubular body during the ligation work, so that the workability is excellent.

Figure 14A:
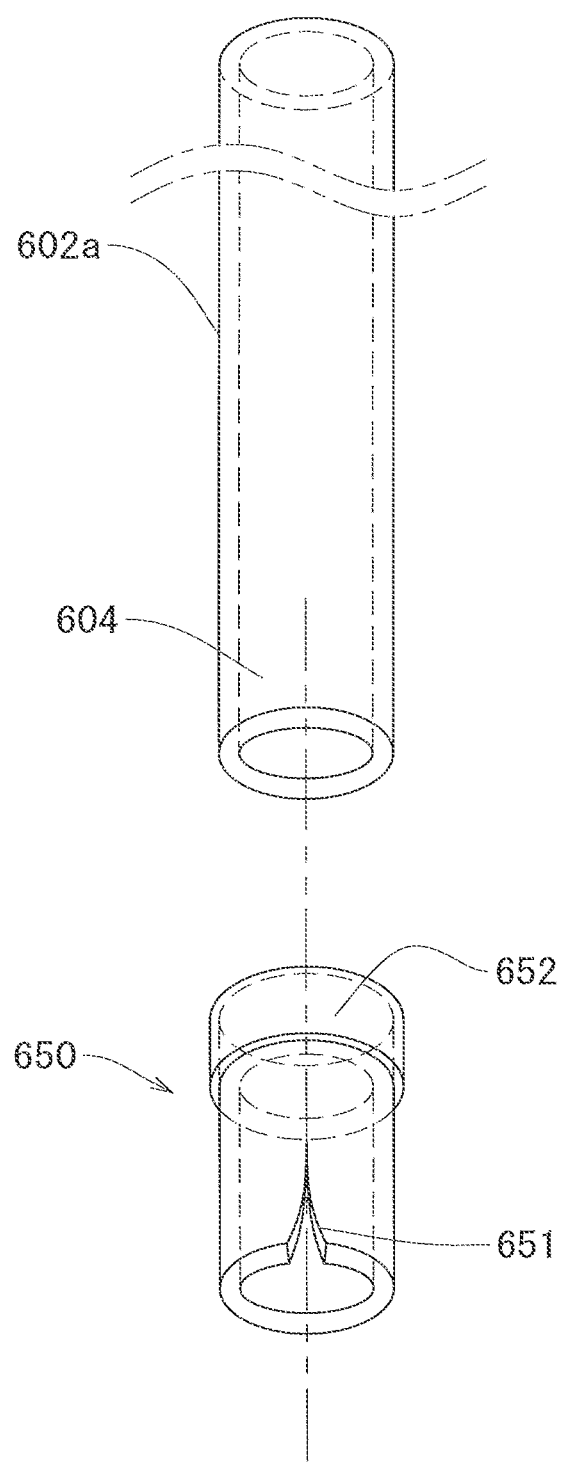
FIGS. 14A and 14B are perspective views of an example of a ligation device including a main body part and an attachment body.
Figure 14B:
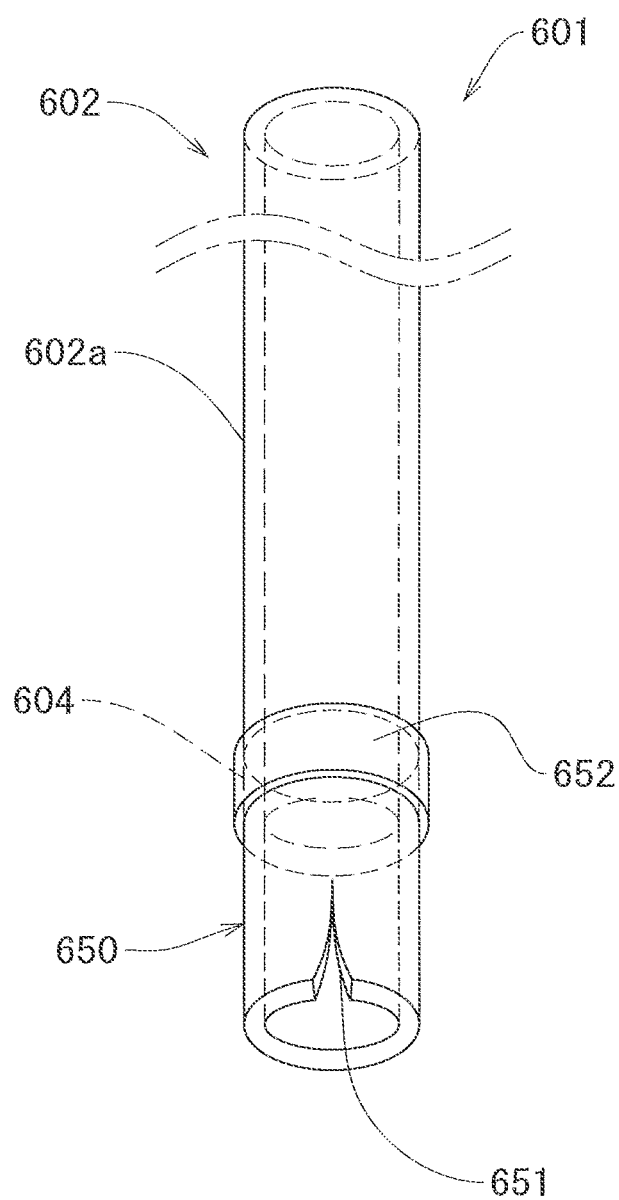

In each of the embodiments described above, as illustrated in FIGS. 14A and 14B, a tubular body 602 may have a structure in which an attachment body 650 including a locking part 610 having a structure similar to that of the locking part in each of the embodiments is attached to a distal end part 604 of a main body part in a main body part 602*a* having a hollow tubular shape. For example, in a ligation device 601 of FIGS. 14A and 14B, the attachment body 650 including a locking groove 651 similar to the locking part 10 according to the first embodiment is attached to the distal end part 604 of the main body part 602*a*. The attachment body 650 has a hollow cylindrical shape, includes a fitting part 652 into which the distal end part 604 of the main body part 602*a* can be fitted on a proximal end part, and includes the locking groove 651 provided by cutting from a distal end surface 653 to the proximal direction on a distal end part. The fitting part 652 is configured so that the inner diameter of the fitting part 652 substantially matches the outer diameter of the distal end part 604 of the main body part 602*a*. Then, the distal end part 604 of the main body part 602*a* is inserted and fitted into the fitting part 652 of the attachment body 650 to attach the attachment body 650 including the locking groove 651 as the locking part. The ligation device 601 can be used by a similar method as the ligation device 1 according to the first embodiment.

With such a configuration, the ligation device according to the present invention can be obtained, for example, by attaching the attachment body to a commercially available tube, and thus, the manufacturing cost can be reduced. The attachment mode of the attachment body 650 to the main body part 602*a* is not limited to the above, and various attachment modes are possible. For example, a tapered structure may be adopted to obtain versatility corresponding to various diameters of the tubular body. Further, the locking part can also have various structures, including a structure similar to that described in each of the above embodiments.

In each of the embodiments described above, a proximal locking part may be provided at the proximal end part of the tubular body. That is, if the structure of each of the locking parts mentioned above is also provided at the proximal end part, the first end part of the string-shaped body can be locked to the proximal locking part, and thus, there is no need to perform fixing with forceps or a clip. At this time, the locking part and the proximal locking part do not necessarily have the same structure. Further, a structure may be adopted in which a cap is provided at the proximal locking part and the string-shaped body is fixed by tightening the cap. A conventional structure can be appropriately adopted for the structure of the proximal locking part such as the cap.

The ligation device according to the present invention can be used for living body vessels such as blood vessels, intestinal tracts, and ureters, as well as various ligation targets such as various types of organs and instruments that need to be temporarily ligated. More specifically, the ligation device can be used in various surgical operations such as ligation of arteries during CEA and OPCABG, fixation of catheters and cannulas, and sheath fixation in stent graft interpolation for aortic aneurysm.

INDUSTRIAL APPLICABILITY

The present invention can be utilized in a ligation device used for ligating a ligation target such as a living body vessel, an organ, or an instrument in a surgical operation.

REFERENCE SIGNS LIST

1 Ligation device
2 Tubular body
3 Proximal end part
3a Proximal opening
4 Distal end part
4a Distal opening
4b Distal end surface
5 Hollow part
10 Locking part
11 Locking groove
20 String-shaped body
21 First end part
22 Second end part
212 Notch
311 Locking groove
312 Protruding part
411 Winding part
511 Locking hollow part
511a Large diameter part
511b Small diameter part
512 Opening part
513 Groove part
602 Tubular body
602a Main body part
650 Attachment body
V Blood vessel (target)

The invention claimed is:

1. A ligation device comprising:
a tubular body having a tubular shape and including a hollow part into which a string-shaped body can be inserted,
the tubular body including a proximal opening at a proximal end part and a distal opening at a distal end part, respectively,
the proximal opening and the distal opening communicating with each other via the hollow part of the tubular body,
the ligation device capable of ligating a target by fixation of the string-shaped body pulled in a proximal direction to the tubular body in a state where the string-shaped body is wound around a target and the target is pressed against a side of the distal end part of the tubular body, wherein
a side of a first end part of the string-shaped body can be inserted into the hollow part,
the tubular body includes, on the distal end part, a locking part capable of locking a side of a second end part of the string-shaped body, after the string-shaped body is wound around the target, in a state where the side of the first end part of the string-shaped body is inserted into the hollow part,
the locking part includes a locking groove configured to lock the string-shaped body by press-fitting,
a notch formed by cutting a peripheral surface of the tubular body is provided at the distal end part of the tubular body,
the locking groove is provided from an end part of the notch, and
the notch and the locking groove do not extend to a distal end surface of the tubular body.

2. The ligation device according to claim 1, wherein the tubular body includes a main body part having a tubular shape and an attachment body attached to a distal end part of the main body part, and the locking part is provided in the attachment body.

* * * * *